US00PP35803P2

(12) United States Plant Patent
Evison

(10) Patent No.: US PP35,803 P2
(45) Date of Patent: May 14, 2024

(54) ***CLEMATIS* PLANT NAMED 'EviGsy151'**

(50) Latin Name: ***Clematis patens* x *Clematis viticella***
Varietal Denomination: EviGsy151

(71) Applicant: Raymond J. Evison Ltd., Vale (GB)

(72) Inventor: Raymond J. Evison, Vale (GB)

(73) Assignee: Raymond J. Evison Ltd., Guernsey (GB)

( * ) Notice: Subject to any disclaimer, the term of this patent is extended or adjusted under 35 U.S.C. 154(b) by 0 days.

(21) Appl. No.: 18/219,091

(22) Filed: Jul. 7, 2023

(30) Foreign Application Priority Data

May 10, 2023 (QZ) ..... PBR 2023/1037

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Penny J. Aguirre

(57) ABSTRACT

A new cultivar of hybrid *Clematis* plant named 'EviGsy151' that is characterized by its large sized flowers, its vibrant purple-blue flowers with a vertical pink central band on the tepals, and vibrant red anthers, its compact plant habit, its very floriferous blooming habit, its good vigor with ease of growth, its good suitability for growing in gardens and containers.

2 Drawing Sheets

Botanical classification: *Clematis patens* x *Clematis viticella.*
Variety denomination: 'EviGsy151'.

CROSS REFERENCE TO A RELATED APPLICATION

This application claims priority to European Community Plant Variety Office (CPVO) Plant Breeder's Rights Application No. 2023/1037 filed on May, 10, 2023, the entire contents of which is incorporated by reference herein.

BACKGROUND OF THE INVENTION

The present invention relates to a new and distinct cultivar of *Clematis* of hybrid origin and will be referred to hereafter by its cultivar name 'EviGsy151'. 'EviGsy151' is an herbaceous perennial grown for use as a landscape and container plant.

'EviGsy1l51' derived from an ongoing breeding program by the Inventor at his nursery in Guernsey, United Kingdom. The goal of the program was to select a new cultivar of *Clematis* with a compact plant habit, a floriferous blooming habit, and uniquely colored large flowers. 'EviGsy151' was selected as a single unique plant in May of 2019 and arose from a controlled cross made in June of 2014 between unnamed proprietary plants of *Clematis patens* x *Clematis viticella* from the Inventor's breeding program as both the female and male parents.

Asexual propagation of the new cultivar was first accomplished by softwood stem cuttings under the direction of the Inventor in May of 2019 in Guernsey, United Kingdom. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'EviGsy151' as a unique cultivar of *Clematis.*

1. 'EviGsy151' exhibits large sized flowers.
2. 'EviGsy151' exhibits vibrant purple-blue flowers with a vertical pink central band on the tepals, and vibrant red anthers.
3. 'EviGsy151' exhibits a compact plant habit.
4. 'EviGsy151' exhibits a very floriferous blooming habit.
5. 'EviGsy151' exhibits good vigor with ease of growth.
6. 'EviGsy151' exhibits good suitability for growing in gardens and containers.

The female parent of 'EviGsy151' differs from 'EviGsy151' in having flower tepals that are less blue in color and a less compact plant habit. The male parent of 'EviGsy151' differs from 'EviGsy151' in having flower centers with yellow anthers. 'EviGsy151' can be most closely compared to the *Clematis* cultivars 'Evipo041' (U.S. Plant Pat. No. 24,171) and 'Evipo019' (U.S. Plant Pat. No. 16,069). 'Evipo041' is similar to 'EviGsy151' in having purple flowers with a vertical center band on the tepals and a center of red stamens. 'Evipo041' differs from 'EviGsy151' in having flowers that are less blue in color and have a less compact plant habit. 'Evipo019' is similar to 'EviGsy151' in plant habit and in having a center of red stamens. 'Evipo019' differs from 'EviGsy151' in having flower tepals that have less red tones and lacks a vertical central band.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Ray Evison *Clematis*, RHS Plants, Thorncroft *Clematis*, Thompson & Morgan, Hayloft Plants, Burford Garden Center, Van Meuwen, Crocus, Suttons, AIPH, QVC UK, Primrose, Linkedln (Peter van Rijssen), Cowell's Garden Center, ITVX, Dobies, Gardener's World, Harrod Horticultural, Horticulture Week (Chelsea Flower Show), and Sheridan Nurseries.

BRIEF DESCRIPTION OF THE DRAWINGS

The accompanying color photographs illustrate the overall appearance and distinct characteristics of the new *Clematis*. The photographs were taken of a 2.5-year-old plant as grown in a conventional greenhouse in 17-cm containers in Guernsey, United Kingdom.

The photograph in FIG. 1 provides a side view of 'EviGsy151' in bloom.

Figure 1:
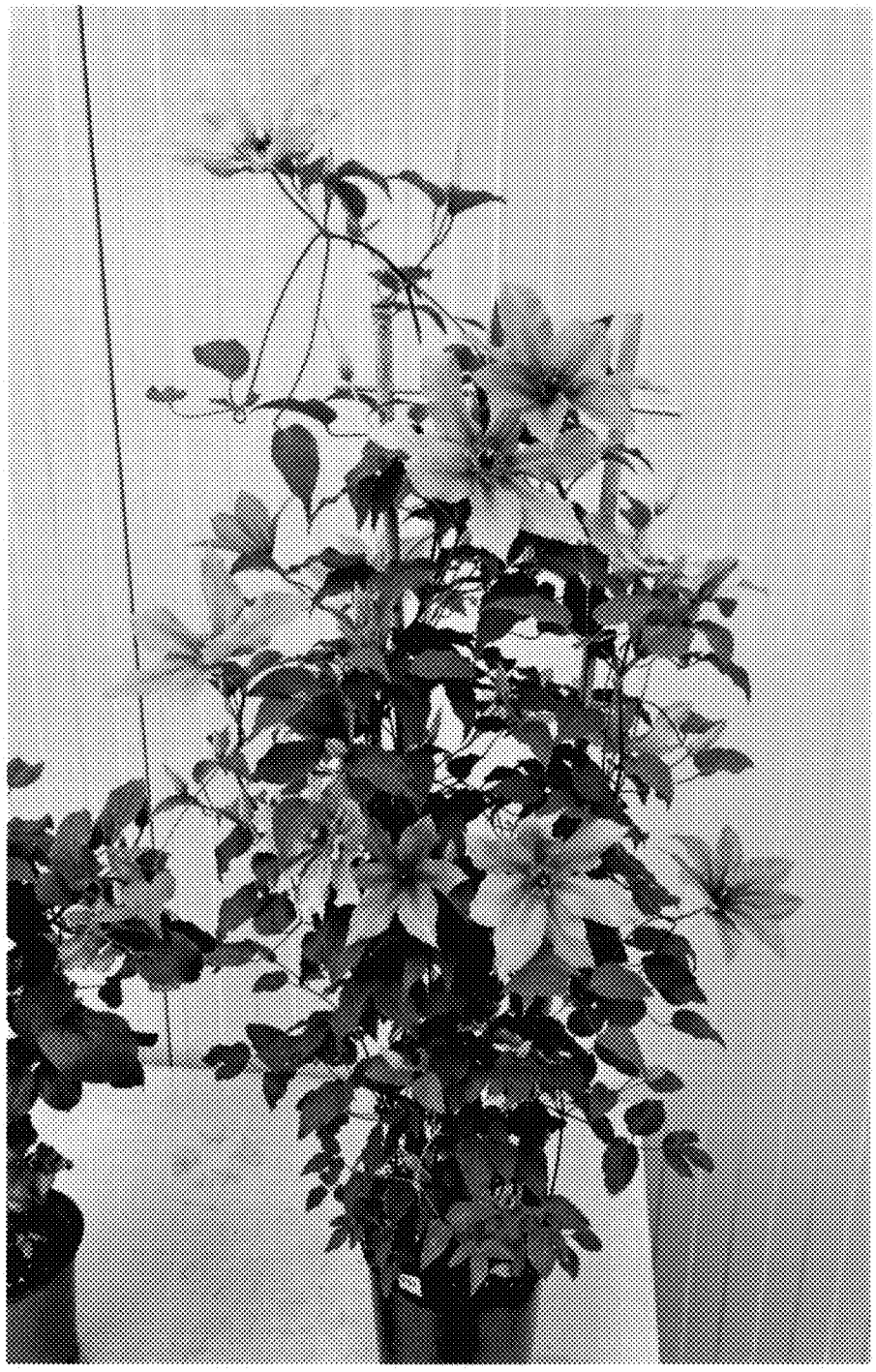
Figure 2:
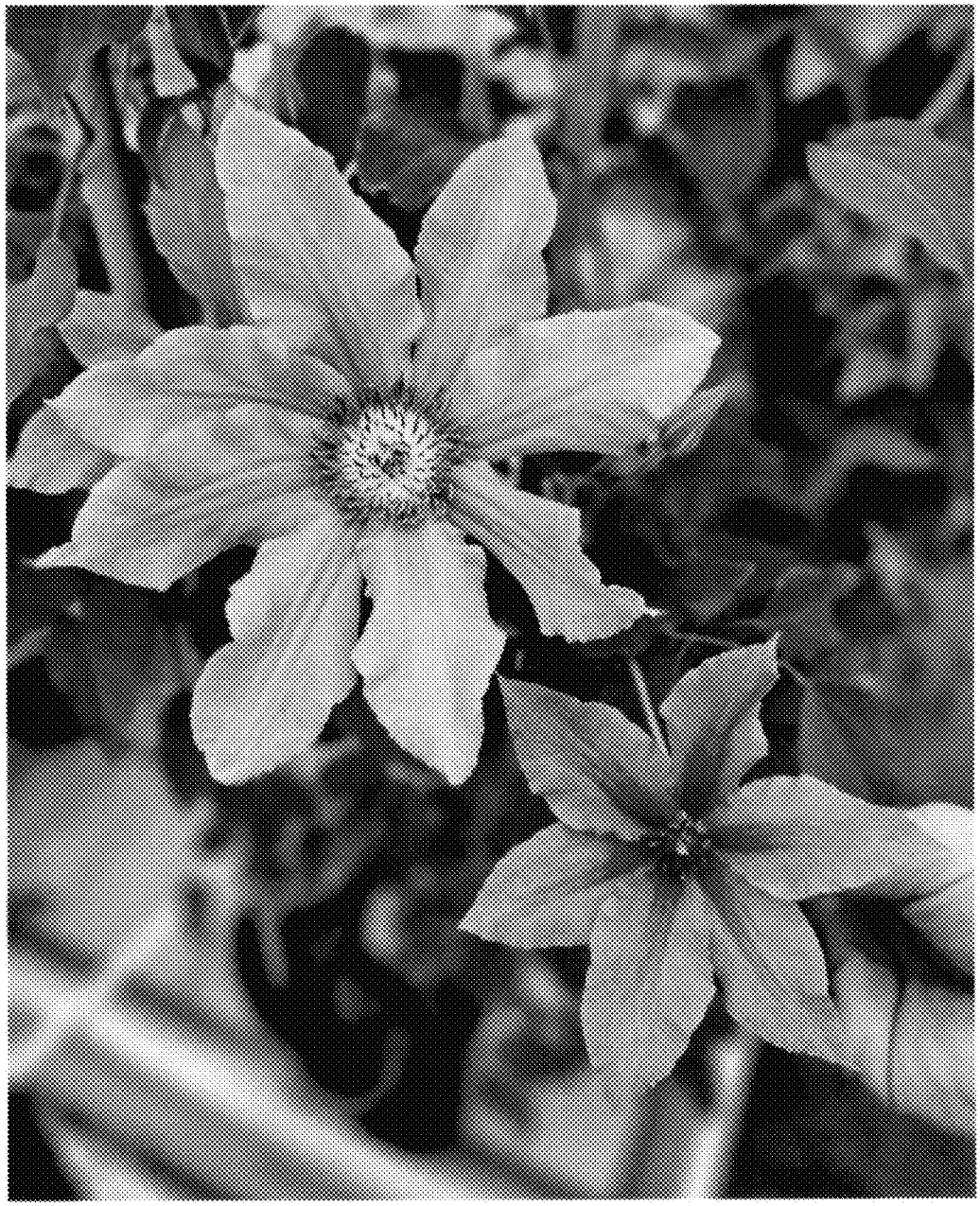

The photograph in FIG. 2 provides a close-up view of a mature flower (top) and young flower (bottom) of 'EviGsy151'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of 2.5-year-old plants as grown in a conventional greenhouse in 17-cm containers in Guernsey, United Kingdom. The phenotype of the new cultivar may vary with variations in environmental, climatic, and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—May/June to August/September in the United Kingdom.

*Plant type*.—Deciduous woody perennial.

*Plant habit*.—Climber, compact.

*Height and spread*.—Season's growth an average of 80 cm in height and 50 cm in spread.

*Cold hardiness*.—At least to U.S.D.A. Zone 6.

*Diseases and pests*.—No susceptibility to diseases or pests has been observed.

*Root description*.—Fleshy, NN155A with a layer of N199C.

*Propagation*.—Softwood stem cuttings.

*Root development*.—An average of 3 to 4 weeks for root initiation and another 4 to 6 weeks to produce a rooted plant, 30 weeks for a mature plant in a P12 container.

*Growth rate*.—Moderate.

Branch description:

*Branch shape*.—Round.

*Branch color*.—Young; 144A to 144B, flushed with 183B, mature; 183B, wood; 183B.

*Branch size*.—Basal stems; 75 cm to 1.5 m in length, 2 mm in diameter, lateral branches; 30 cm in length and 3 mm in width.

*Branch surface*.—Young and mature; slightly glossy and sparsely pubescent, older stems and wood; glabrous, slightly glossy.

*Branch strength*.—Strong and flexible.

*Branch angle*.—Upright.

*Branching*.—Moderately and freely branching, main; 5, lateral; 2 per main branch.

*Internode length*.—Average of 7 cm.

Foliage description:

*Leaf arrangement*.—Opposite, ternate.

*Leaf division*.—Compound.

*Leaf quantity*.—Average of 10 per stem.

*Leaf shape*.—Broadly ovate in outline, single leaves on lateral branches ovate.

*Leaf size*.—Average of 16 cm in length and 14 cm in width.

*Leaflet quantity per compound leaf*.—3.

*Leaflet shape*.—Ovate.

*Leaflet base*.—Rounded to obtuse.

*Leaflet apex*.—Acute.

*Leaflet venation*.—Pinnate, upper surface; 144B, lower surface; 137B.

*Leaflet margins*.—Entire, unlobed.

*Leaflet surface*.—Upper surface; glabrous, moderately glossy, lower surface; glabrous, matte.

*Leaflet size*.—Average of 7.3 cm in length and 4.4 cm in width.

*Leaflet color*.—Young upper surface; 144A, young lower surface; 146B, mature upper surface; 137B, mature lower surface; 137C.

*Petioles*.—Up to 9 cm in length, 2 mm in diameter, strong, sparsely covered with pubescence, slightly glossy surface, color; 144A, flushed with 183B.

*Petiolules*.—Up to 4.5 cm in length, 1.5 mm in diameter, strong, sparsely covered with pubescence, slightly glossy surface, color; 144A, flushed with 183B.

Inflorescence description:

*Inflorescence type*.—Solitary.

*Inflorescence arrangement*.—Terminal on old wood and young shoots.

*Inflorescence size*.—Up to 12.3 cm in width, 3 cm in depth.

*Flower quantity*.—Freely flowering, average of 7 open flowers and 12 buds per plant.

*Flower aspect*.—Outward, rotate.

*Flower shape*.—Round and star-shaped.

*Peduncles*.—Up to 5.2 cm in length and 3 mm in diameter, 145B to 145C in color, round in shape, surface is glabrous, strong.

*Pedicels*.—Average of 2 cm in length, 2 mm in diameter, 145B to 145C in color, round in shape, surface is glabrous, moderately strong.

*Flower buds*.—Upright to outward, ovoid in shape, 4.4 cm in length, 1.9 cm in diameter, color; 145B, lightly flushed with N77D, surface is matte and densely covered with pubescence.

*Flower fragrance*.—None.

*Lastingness of the flowers*.—Self-cleaning, lasts 10 days.

*Tepals*.—8, elliptic in shape, curved downward and slightly carinate, acuminate apex, acute base, entire margins that are moderately undulate, both surfaces glabrous and satiny, color; when opening upper surface; N88C to N88D, margins N87A, central band 78A, mid-rib 71B, when opening lower surface; N88C to N88D, mid-rib 145C to 145D, when fully open upper surface; N88B, margins N88C, central band 78A to 78B, mid-rib a blend of 78B and N88B to N88C, when fully open lower surface; N88C to N88D, mid-rib 145C to 145D.

*Tepal size*.—Average of 5.7 cm in length, 3.4 cm in width.

*Calyx*.—6 mm in length and diameter, 144B in color, rounded, rotate, surface is pubescent.

Reproductive organs:

*Gynoecium*.—Pistils; 70 to 80, stigma; not distinguishable, style; 1.1 cm in length, 146D in color, ovary; superior, 144D in color, 1 mm in diameter.

*Androecium*.—Stamens; 150, filaments; 6 mm in length, 149D in color, anthers; 6 mm in length, basifixed, narrow oblong in shape, 71A in color, pollen; none observed.

*Seed*.—Seed head; up to 4 cm in diameter, half orbicular in shape, 50% of the pistils might set seed by open pollination, seed; average of 25 per seed head, 4 mm in length and width, 71A, 144B in color, pubescent, seed style; up to 2 cm in length, 144B in color, surface 164D in color, seed stigma; thin and 200A in color.

It is claimed:

1. A new and distinct cultivar of *Clematis* plant named 'EviGsy151' as herein illustrated and described.

* * * * *